United States Patent
Wilkerson

[11] Patent Number: 5,902,259
[45] Date of Patent: May 11, 1999

[54] THERAPEUTIC ANKLE ORTHOSIS

[76] Inventor: Gary Wilkerson, 617 N. 30th St., Paducah, Ky. 42001

[21] Appl. No.: 08/578,968

[22] Filed: Dec. 27, 1995

[51] Int. Cl.[6] ..................................................... A61F 5/00
[52] U.S. Cl. ................................ 602/27; 602/16; 602/23; 602/65
[58] Field of Search .................................. 602/5, 16, 23, 602/27–29; 128/882

[56] References Cited

U.S. PATENT DOCUMENTS

| | | | |
|---|---|---|---|
| 4,556,054 | 12/1985 | Paulseth | 602/27 |
| 4,719,926 | 1/1988 | Nelson | 602/27 |
| 5,031,607 | 7/1991 | Peters | 602/27 |
| 5,044,360 | 9/1991 | Janke | 602/27 X |

Primary Examiner—Richard J. Apley
Assistant Examiner—Kim M. Lee
Attorney, Agent, or Firm—Harry A. Pacini

[57] ABSTRACT

A therapeutic ankle orthosis including overlapping medial and foot shells pivotally interconnected to permit pivotal foot movement about the talocrural joint with the overlapping portions of the medial and foot shells secured together to protect against ankle ligament injury from rotation of the foot and leg in opposite directions in the horizontal plane, said ankle orthosis includes interactive effective means for accentuating the compression effect on the soft tissues surrounding the fibular malleolus for control of ankle swelling.

33 Claims, 6 Drawing Sheets

FIG. 6B

THERAPEUTIC ANKLE ORTHOSIS

BACKGROUND OF THE INVENTION

At the outset a distinction is to be made between functional ankle braces and therapeutic ankle orthoses. An ankle brace is designed to limit the range of side-to-side foot motion during stressful functional activities. An ankle orthosis, on the other hand, serves as a functional ankle brace during the transitional period between resolution of acute sprain symptoms and complete restoration of normal ankle function and, at the same time, therapeutically treats and controls residual sprain symptoms.

An example of an ankle brace of the prior art is that disclosed in U.S. Pat. No. 5,069,202. Its structure includes a foot shell pivoted to a leg shell which comprises lateral and medial uprights connected by an anterior band. Adjustable strap means are included for holding these components in operative position on the leg, ankle and foot. Another form of ankle brace is disclosed in U.S. Pat. No. 5,199,941 which includes medial and lateral shells connected to a foot shell, though without a pivotal joint between them. A therapeutic ankle orthosis is disclosed in U.S. Pat. No. 4,556,054 and includes a foot shell and a leg cuff interconnected by appropriate adjustable straps.

The prior art disclosure perhaps most pertinent to the present invention is German Gebrauschmuster (hereinafter referred to as the "Petty" patent) No. 68814157.8, published Feb. 9, 1989. It is intended to function therapeutically during recovery from acute sprain symptoms and at the same time to brace the ankle to limit the maximum range of side-to-side foot motion. The therapeutic functions include compression and joint stabilization. The Petty patent teaches a foot shell pivotally and slidably connected to the lower end of lateral and medial shells by means of a post in a curved slot, with the components held together by adjustable strap means. The lateral shell includes an aperture for encircling the fibular malleolus and an inner pad for compression. The pad is not U-shaped, though pads of that configuration are known from such prior art patents as my U.S. Pat. No. 4,590,932 to disperse edema upwardly from those regions around the fibular malleolus where excess fluid accumulates.

The most common mechanism causing ankle ligament injury is inversion or turning inward of the sole of the foot. However, there is an associated mechanism which involves rotation of the foot and leg in opposite directions in a horizontal plane, referred to as adduction of the foot or internal foot rotation combined with external leg rotation. Prior art ankle braces emphasize means for restraining inversion of the foot but do little to protect against external rotation of the leg upon a foot that is fixed to the ground.

In the Petty patent referred to above, the articulation of the foot shell with respect to the lateral shell by means of a curved slot and rivet allows for a combination of rotational and gliding movement between the components. The curvature of the slot does not correspond to the functional axis of the upper ankle joint, namely the talocrual joint. Rotation of the foot and leg in opposite directions in a horizontal plane would result in a spreading apart of the lateral and foot components of the Petty patent along the anterior margin of the overlapped areas. Such a design does not provide resistance to rotary ankle motion within the horizontal plane.

SUMMARY OF THE INVENTION

External compression for control of edema has traditionally been provided by elastic wraps. Wrapping the ankle with elastic material has the undesirable effect of producing generalized pressure over the entire surface of the wrapped extremity. Resolution of ankle edema is greatly facilitated by a focal compression effect that compacts injured soft tissues, while leaving adjacent tissues uncompressed. This focal compression effect can be maximized by using specific strapping configurations and shell contouring. Strap tension over the brace shells results in the production of pressure against selected anatomical locations on the extremity. The interaction of the strapping configuration and shell configuration maximizes conformity of the U-pad to anatomical contours, thereby maximizing the edema drainage effect.

The therapeutic ankle orthosis of the invention includes an extended lateral shell having an aperture for receiving the fibular malleolus and having a lower end portion extending downwardly beneath that aperture. An extended medial shell is adapted to fit beneath and upwardly above the tibial malleolus. A foot shell is adapted to underlie the rear foot and extend forwardly, optionally beyond the mid-tarsal joints, and has an upper medial side portion extending upwardly to overlap the lower end portion of the medial shell. Pivoting means connect the lower end portion of the medial shell to the side portion of the foot shell permitting ankle movement of the foot shell relative to the medial shell about an axis substantially coincident with the functional axis of the talocrual joint. Optionally, locking means may be included for selectively preventing ankle movement of the foot shell relative to the medial shell. Securing means may be provided for holding together the overlapping end portion of the medial shell and the side portion of the foot shell forwardly of the pivot means to resist ankle inversion and eversion. Adjustable strap means are included for holding the shells in operative position on the leg and ankle and foot.

The lateral shell may be contoured generally to fit the lower leg and ankle. A U-pad is secured to the inside of the medial shell and a pad 63 having a shape matching that of the medial shell and having an aperture to receive the tibial malleolus may be secured to the inside of the medial shell. The medial shell lower end portion may be overlapped by the foot shell side portion. The pivot means may be a rivet fixed to the medial shell end portion and extending outwardly through a hole in the overlapping medial foot shell side portion and having a head holding the overlapping side and end shell portions together.

Optionally, a curved slot may be formed in either an overlapping medial shell end portion or the foot shell side portion. The curve of the slot may be centered about the axis of the pivot means. One end of the slot may be approximately horizontally forward of the pivot means axis and the other end of the slot should be at least about 45° downwardly and forwardly of the pivot means axis when the leg and foot is horizontal and vertical, respectively. The slot may be formed in the medial shell lower end portion and the lower end portion may be overlapped by the foot shell side portion.

An optional locking means may comprise a removable locking screw extending through the slot at one end thereof into threaded engagement with the overlapping medial shell end portion and foot shell side portion. When the slot is formed in the foot shell side portion and the lower end medial shell portion is overlapped by the outside of the foot shell side portion, the removable locking screws are in threaded engagement with the medial shell end portion.

An optional securing means may comprise a post affixed to that overlapping shell portion in which the curved slot is not formed. This post may extend through the slot intermediate the ends thereof when the leg and foot are vertical and horizontal, respectively. On the outer end of the post there may be a cap for holding the shell portion in which the slot is formed against the other shell portion. When the slot is formed in the foot lateral shell side portion and the medial shell lower end portion is overlapped by the inside of the foot shell side portion, the post is then affixed to the medial shell lower end portion.

The strap means may include a first strap fixed at one end of a forward portion of the foot shell and threaded through slots in the lateral shell and adjustably secured at the opposite end to buckling means above the overlapping shell portions. A second strap may be provided which is fixed at one end to a rearward portion of the foot shell and threaded through slots in the lateral shell and adjustably securable as its opposite end to the buckling means. Alternatively, a single continuous strap may be threaded through slots in the lateral shell, attached at one end to a forward portion of the foot shell and the other end attached to a rearward portion of the foot shell. Because the alternative strap configuration would not encircle the leg, an additional circumferential strap, with buckling means for adjustable strap tension, would be added above the lateral shell aperture and above the medial overlapping shells to compress the medial and lateral shells against the ankle and leg. There may be a circumferential leg strap affixed at one end to the upper portion of the medial side shell which would encircle both shells and be adjustably secured to itself by means of hook and pile fastener.

The lateral shell may be movable up and down and forward and rearward, with the straps sliding in their respective lateral shell slots, to locate the lateral shell in a selected position relative to a user's fibular malleolus. The X-straps may be affixed to the underside of the lateral side of the forward and rearward portions of the foot shell. The buckling means for the first and second straps may overlie the medial shell.

The shells are preferably semi-rigid, by which is meant that they are stiff enough so that the foot shell, for example, does not significantly lose its foot-contoured shape under normal maximum adult weight, but are flexible enough to be depressed to exert extra localized pressure against the ankle behind a tightly fitted strap.

BRIEF DESCRIPTION OF THE DRAWINGS

When a number is used in the following descriptions it is intended to include alternative views, as for example, FIG. 2 includes FIG. 2A, 2B, etc.

DESCRIPTION OF THE PREFERRED EMBODIMENT

Referring first to FIGS. 1 to 4, the therapeutic ankle orthosis of the invention includes three semi-rigid shells: namely, an extended lateral shell 10, a foot shell 11 and an extended medial shell 12. Each of the shells is of unitary molded plastic construction, optionally of varying thickness to vary the degree of semi-rigidity in different portions of each shell. Polypropylene or polyethylene may be suitable materials for the shells. Each is contoured to fit generally against typical leg, ankle and foot anatomy against which it is disposed during use.

The lateral shell 10 fits against and is contoured to the lateral side of the lower leg and ankle and includes an aperture 13 to receive the fibular malleolus. Optionally, the lateral shell 10, foot shell 11, and medial shell 12 can each be symmetrical about its respective longitudinal axis and therefore be reversible to fit on either the left or the right foot and ankle (FIGS. 1B, 2B and 6B).

Figure 1A:
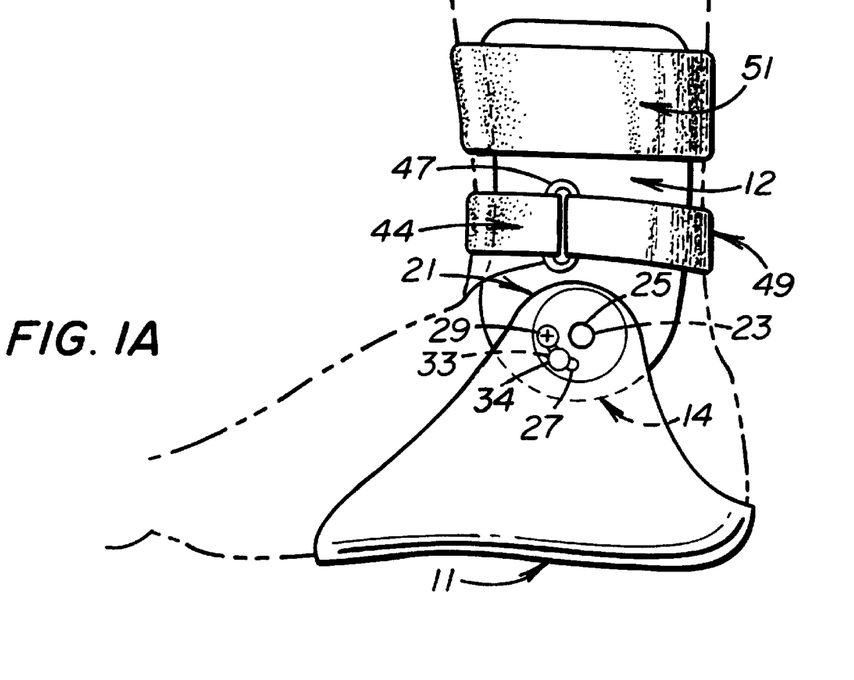
FIG. 1A shows the orthosis locking means in place and fully assembled on a leg and ankle and foot.
Figure 1B:
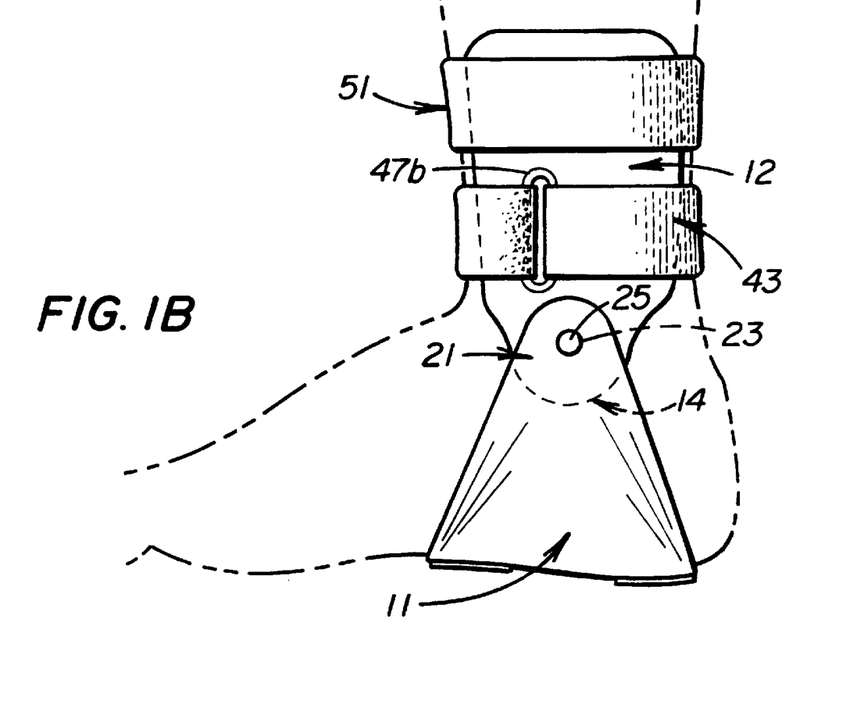
FIG. 1 is an elevation of the therapeutic ankle orthosis of the invention viewed from the medial side showing the foot in horizontal position.
Figure 2A:
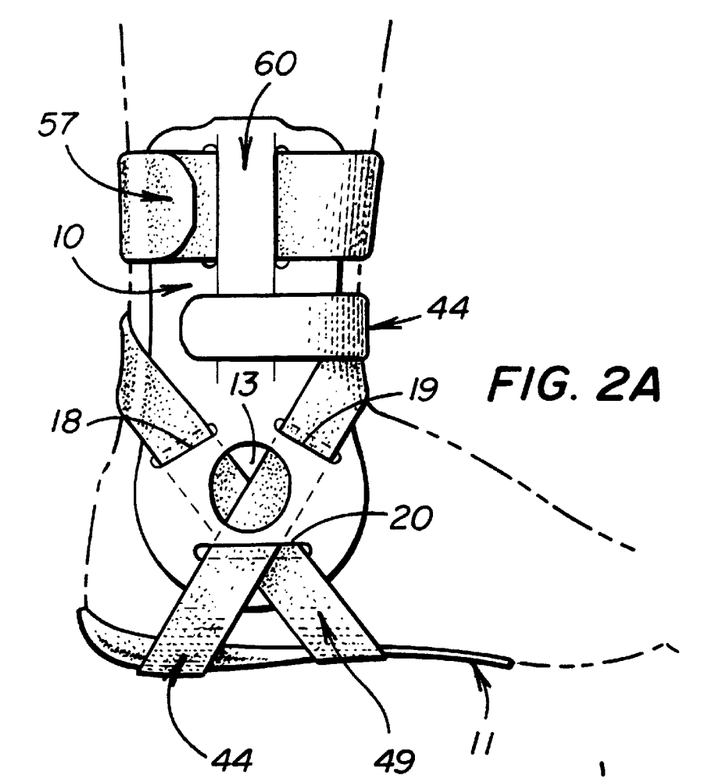
FIG. 2 is an elevation of the lateral side of the assembled therapeutic ankle orthosis of FIG. 1 showing the foot in horizontal position.
Figure 2B:
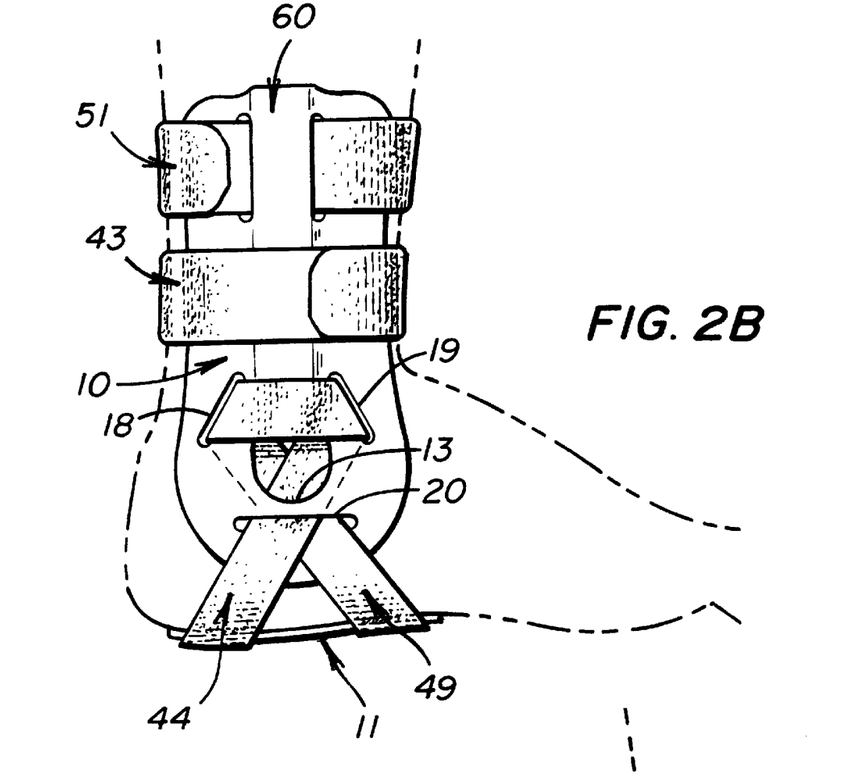

The lateral shell 10 shown in FIGS. 1A and 1B is adapted to fit beneath and upwardly about the fibular malleolus. It has a symmetrical configuration and can be used on either the left or the right ankle. The lateral shell includes a slot 18 and a slot 19. Between and placed below these slots is a wider central slot 20.

Figure 6A:
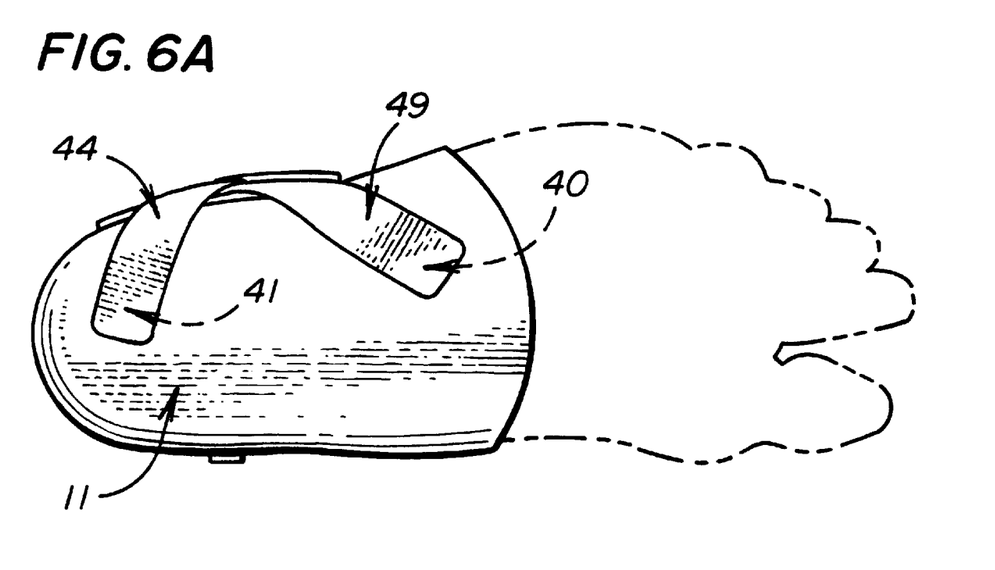
FIG. 6 is a view of the underside of the foot shell of the therapeutic ankle orthosis of the invention showing the connections of certain of the adjustable straps to the foot shell.
Figure 6B:
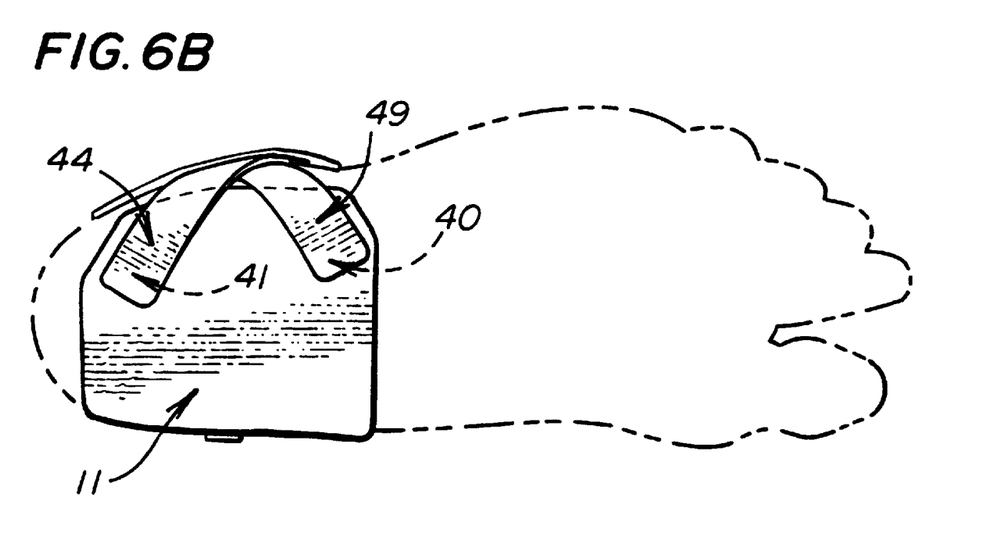

The foot shell 11 is adapted to underlie the rear foot and may extend forwardly beyond the tarsal joint FIGS. 1A and 6A). It is in the form of a contoured stirrup which includes an upper medial side portion 21.

A rivet 23 provides pivot means connecting the lower end portion 14 of the medial shell 12 to the upper side portion 21 of the foot shell 11. The rivet 23 is affixed to the medial shell lower end portion 21 and extends outwardly through a hole in the overlapping foot shell side portion 14. A head 25 on the rivet 23 holds the overlapping side and end shell portions 21 and 14 together and at the same time permits angular movement of the foot shell 11 relative to the medial shell 12 about an axis substantially coincident with the functional axis of the talocrual joint.

Formed in the foot shell side portion 21 is a curved slot 27 centered about the axis of the rivet 23. As shown in FIG. 1, one end of the slot 27 is approximately horizontally forward of the pivot means provided by the rivet 23 and the other end of the slot 27 is at least about 45° downwardly and forwardly of that pivot means axis when the leg and foot are vertical and horizontal, respectively. A removable locking screw 29 extends through the upper end of the slot 27 into threaded engagement with the overlapped medial shell end portion 14. When the locking screw is in place as shown in FIG. 1A, the user cannot pivot the foot shell 11 with respect to the medial shell 12 downwardly to lower the foot. At an appropriate stage in the therapy process when movement of the foot with respect to the leg is permissible, the lock screw 29 may be removed so that the foot can articulate as, for example, downwardly into the position shown in FIG. 3. If desired, the curved slot 27 may extend upwardly above a line horizontal with the axis of the rivet 23 when the leg is vertical and the foot is horizontal to permit the foot to be raised slightly above the horizontal while the leg is vertical.

Figure 4:
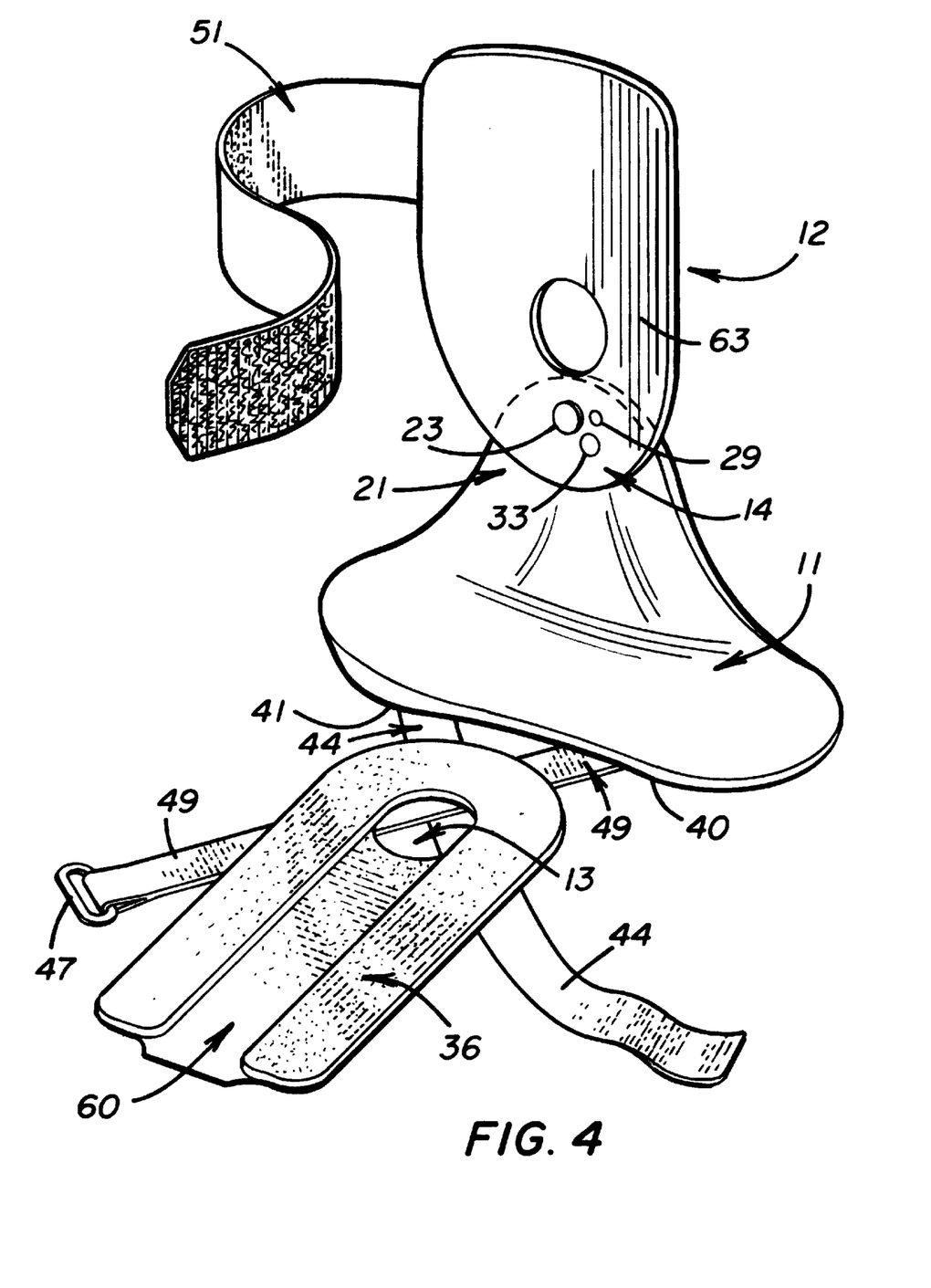
FIG. 4 is a perspective view of certain of the dissembled components of the therapeutic ankle orthosis of the invention.

Holding together the overlapping lower end portion 14 of the medial shell 12 and the side portion 21 of the foot shell 11 is securing means comprising a post 33 extending slidably through the slot 27 intermediate the ends thereof when the leg and foot are vertical and horizontal respectively as shown in FIG. 1A and FIG. 4. A cap 34 is provided on the outer end of the post 33 for holding the medial shell lower end portion 14 against the foot shell side portion 21 for reasons explained hereinafter.

Figure 5:
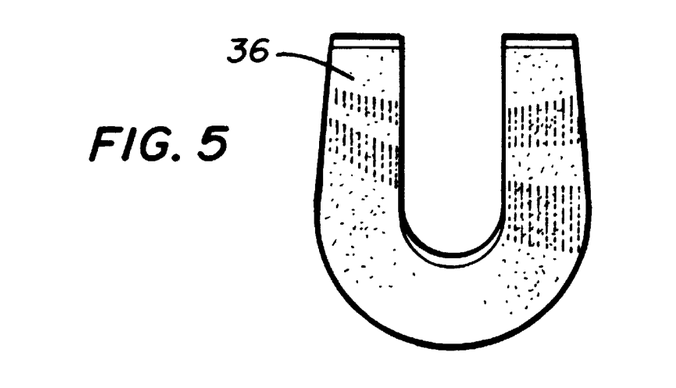
FIG. 5 is a side perspective view of the U-pad to be disposed on the inside of the lateral shell.

Shown in FIG. 5 is a U-pad 36 of self-supporting thermoplastic foam material or a U-shaped fluid-filled capsule having a configuration. It is releasably secured to the inside of the lateral shell 10 by appropriate means such as quick-release hook-and-pile fastener patches sold under the trademark "Velcro®". This U-shaped configuration provides an upwardly open channel for translocation of edema from around the fibular malleolus.

Figure 1C:
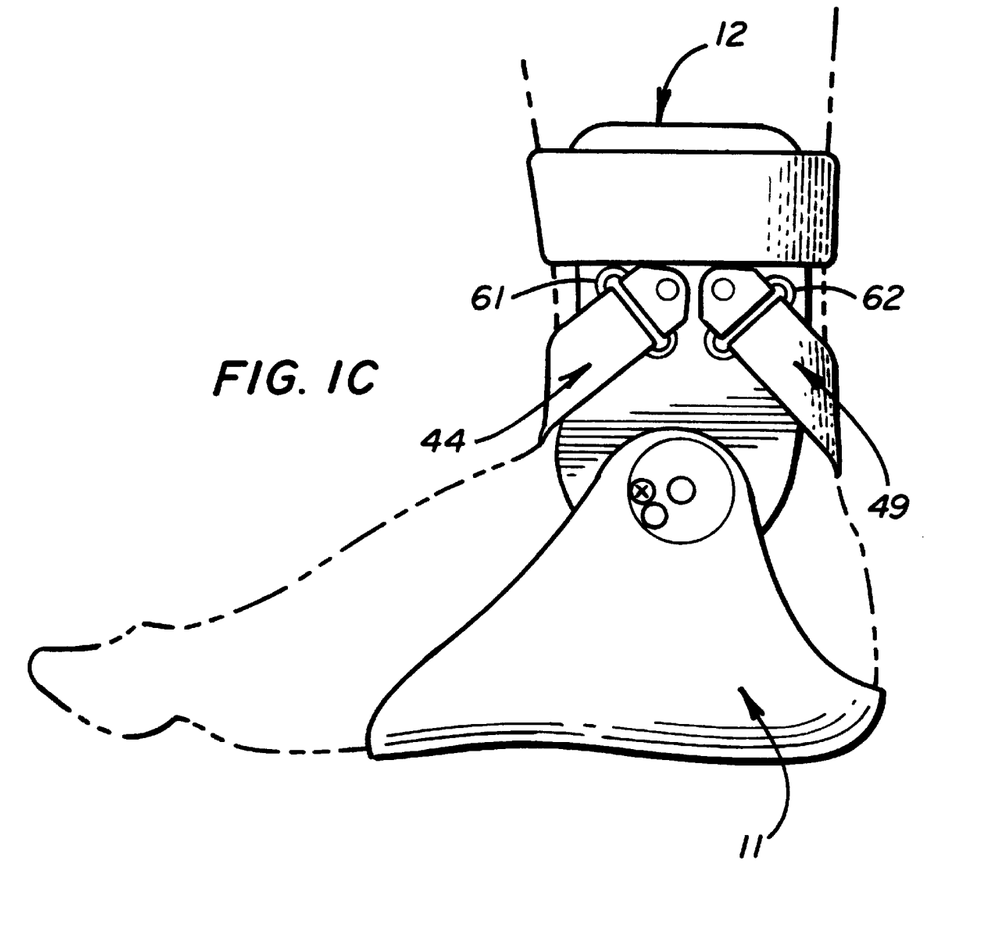

Referring to FIG. 6, the X-strap ends 40 and 41 are fixed to the lateral underside of the forward and rearward portions respectively of the foot shell 11 by means of hook and pile fastener. The forward attachment 40 secures one end of a strap 49 which is threaded through slots 20 and 18 in the lateral shell 10. The strap 49 is connected to a D-ring 47 which provides buckling means positioned above the overlapping shell portions 14 and 21. Secured by the rearward hook and pile fastener attachment 41 is a second strap 44 which is threaded through the slots 19 and 20. The remote end of the strap 44 is passed through the D-ring 47 and can be adjustably tightened by being turned back upon and secured to itself or to the outer surface of the lateral shell 10 with the use of hook-and-pile fastener means. Straps 44 and 49 could also be secured and adjustably tightened by passing them through a pair of D-rings 61 and 62 riveted to the medial shell 12 (FIG. 1C).

Figure 3:
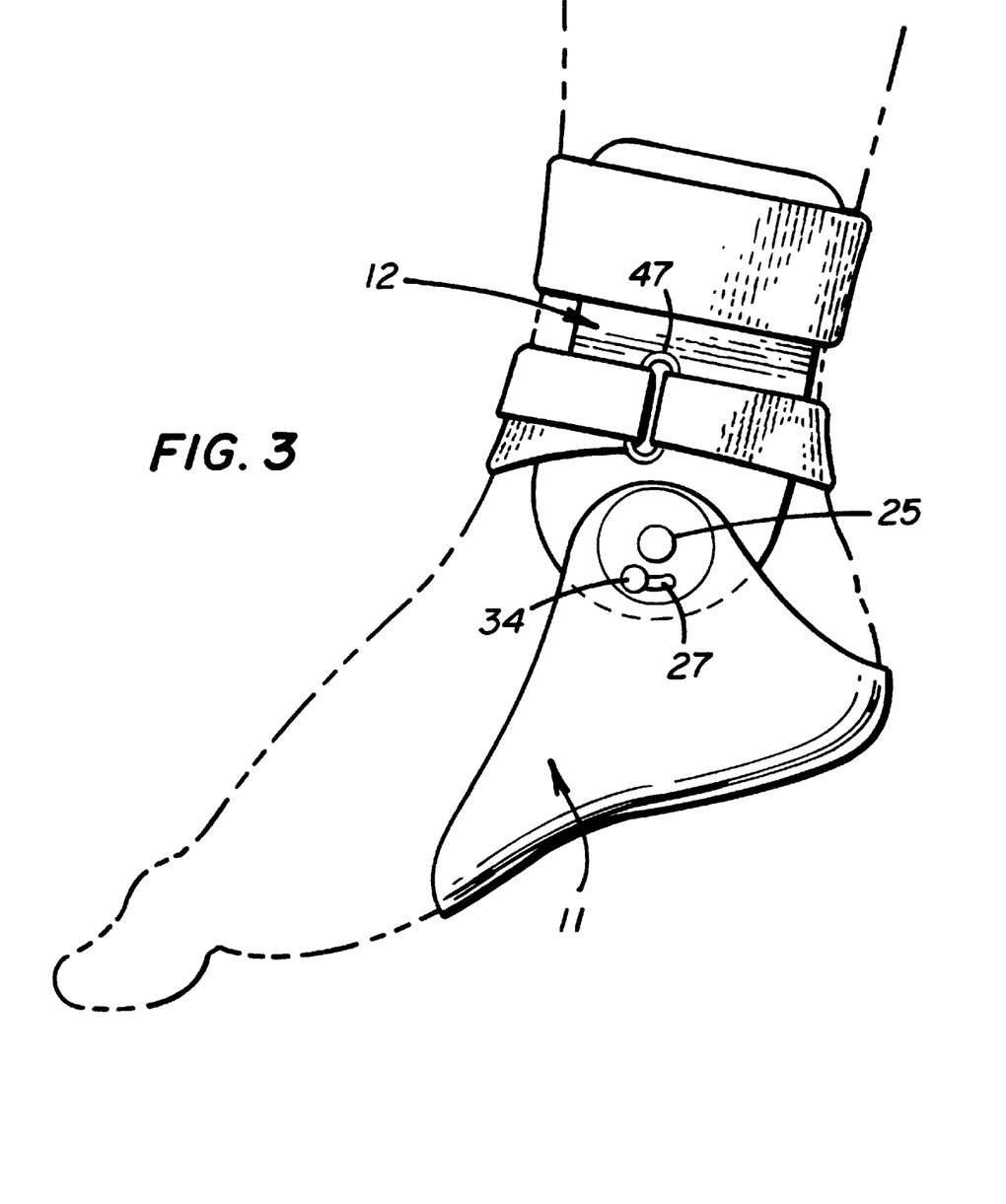
FIG. 3 is an elevation similar to FIG. 1 with the locking means removed and showing the foot turned downwardly.

In use as shown in FIGS. 1A and 3, the D-ring 47 overlies the medial shell 12 spaced above the pivot. By tightening the straps 44 and 49 (or strap 43 on the alternate design) compression can be applied to the lateral shell 10 and thus to the U-pad 36 to compress the ankle directly forwardly and rearwardly of the fibular malleolus which is where edema tends to accumulate as a consequence of an ankle sprain. Alternatively, a single continuous strap may be threaded through slots in the lateral shell, attached at one end to a forward portion of the foot shell and the other end attached to a rearward portion of the foot shell. Because the alternative strap configuration would not encircle the leg, an additional circumferential strap 43, with buckling means 47B for adjustable strap tension, would be added above the lateral shell aperture and above the medial overlapping shells to compress the shells against the ankle and leg (FIG 1B).

A leg strap 51 is affixed at one end by hook and pile fastener to the upper portion of the medial shell. The strap 51 may be adjustably tightened by being secured to itself by suitable hook-and-pile fastener means.

When the ankle orthosis of the invention is strapped to the foot as described above and as shown in FIGS. 1 to 3, several results are achieved. Most importantly, the U-pad 36 directs edema upwardly from around the fibular malleolus and compression is applied precisely where desired forwardly and rearwardly of the fibular malleolus. The lateral shell 10 and the U-pad 36 may be adjustable up and down and forwardly and rearwardly, with the X-strap system 44 and 49 sliding in its respective lateral shell slots 18, 19 and 20 to locate the lateral shell 10 properly relative to the user's fibular malleolus and direct edema upwardly from that area. Edema drainage is facilitated by vertical channel 60 molded into the lateral shell 10. Foot motion may be prevented by selected use of the locking screw 29 or permitted by its removal.

Hence, there is described hereinabove a system for the interactive effect of a U-shaped pad (attached to the inner surface of the lateral shell), lateral semi-rigid shell contoured, said U-shaped pad adjustably positioned in the lateral shell location in relation to the position of the fibular malleolus (the bony prominence on the outer surface of the ankle) and a strapping system for accentuating the compression effect on the soft tissue surrounding the fibular malleolus for control of ankle swelling.

The scope of this invention is to be determined by the following claims rather than the foregoing description of a preferred embodiment.

The foregoing specification describes the embodiments of the present invention shown and/or described. Other embodiments may be described as well. The terms and expressions used serve to describe the invention by example and are not limited to the invention. Differences may be noted, however, said differences do not depart from the scope, metes and bounds of the invention herein described and claimed. Known elements having equivalent function may be used to replace of the specific constructional elements described.

I claim:

1. A therapeutic ankle orthosis comprising:
   (a) an extended lateral shell having a positioning aperture corresponding to the fibular malleolus and having a lower end portion extending downwardly beneath that aperture;
   (b) an extended medial shell adapted to fit beneath and upwardly about the tibial malleolus;
   (c) a foot shell adapted to underlie the rear foot and having an upper medial side portion extending upwardly to overlap the lower end portion of the medial shell;
   (d) pivot means connecting the lower end portion of the medial shell to the side portion of the foot shell permitting angular movement of the foot shell relative to the lateral shell about an axis substantially coincident with the functional axis of the talocrual joint,
   (e) locking means for selectively preventing angular movement of the foot shell relative to the medial shell;
   (f) securing means for holding together the overlapping lower end portion of the medial shell and the side portion of the foot shell forwardly of the pivot means to resist ankle inversion and eversion; and
   (g) adjustable strap means for holding the shells in operative position on the leg and ankle and foot and for applying focal compression to control edema of the ankle.

2. A therapeutic ankle orthosis according to claim 1 wherein the lateral shell is contoured to match the lateral contour of the ankle and generally to fit the lower leg and ankle.

3. A therapeutic ankle orthosis according to claim 1 wherein the medial shell lower end portion overlaps the foot shell side portion.

4. A therapeutic ankle orthosis according to claim 3 wherein the pivot means is a rivet fixed to the foot shell side portion and extending outwardly through a hole in the overlapping medial shell lower end portion and having a head holding the overlapping side and end shell portions together.

5. A therapeutic ankle orthosis according to claim 1 wherein a curved slot is formed in one of the overlapping medial shell lower end portions and the foot shell side portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on a leg and foot and said leg and foot are positioned vertically and horizontally, respectively.

6. A therapeutic ankle orthosis according to claim 5 wherein the slot is formed in the medial shell lower end portion and the lower end portion overlaps the foot shell side portion.

7. A therapeutic ankle orthosis according to claim 5 wherein the locking means comprises removable locking screw extending through the slot at one end thereof into threaded engagement with the other of the overlapping medial shell lower end portion and foot shell side portion.

8. A therapeutic ankle orthosis according to claim 7 wherein the slot is formed in the medial shell lower end portion, said lower end portion overlapping the foot shell side portion, and the removable locking screw is in threaded engagement with the foot shell side portion.

9. A therapeutic ankle orthosis according to claim 5 wherein the securing means comprises a post affixed to the other of the overlapping medial shell lower end portions and the foot shell side portion, the post extending through the slot intermediate the ends thereof when the leg and foot are vertical and horizontal, respectively, and a cap on the outer end of the post for holding that shell portion in which the slot is formed against the other shell portion.

10. A therapeutic ankle orthosis according to claim 9 wherein the slot is formed in the medial shell lower end portion, the lower end portion overlapping the foot shell side portion, and the post is affixed to the foot shell side portion.

11. A therapeutic ankle orthosis according to claim 1 which includes a U-pad disposed beneath and upwardly about the aperture of the lateral shell and having a vertical channel to facilitate edema drainage during application of focal compression.

12. A therapeutic ankle orthosis according to claim 1 which includes a pad on the inside of the medial shell.

13. A therapeutic ankle orthosis according to claim 1 wherein the shells are semi-rigid.

14. A therapeutic ankle orthosis comprising:
 (a) an extended lateral shell having a positioning aperture corresponding to the fibular malleolus and having a lower end portion extending downwardly beneath that aperture;
 (b) an extended medial shell adapted to fit beneath and upwardly about the tibial malleolus;
 (c) a foot shell adapted to underlie the rear foot and having an upper medial side portion extending upwardly to overlap the lower end portion of the medial shell;
 (d) pivot means connecting the lower end portion of the medial shell to the side portion of the foot shell permitting angular movement of the foot shell relative to the lateral shell about an axis substantially coincident with the functional axis of the talocrual joint;
 (e) locking means for selectively preventing angular movement of the foot shell relative to the medial shell;
 (f) securing means for holding together the overlapping lower end portion of the medial shell and the side portion of the foot shell forwardly of the pivot means to resist ankle inversion and eversion; and
 (g) adjustable strap means for holding the shells in operative position on the leg and ankle and foot wherein the strap means comprises a strap fixed at one end to a forward portion of the foot shell and threaded through first slots in the lateral shell, a second strap fixed at one end to a rearward portion of the foot shell and threaded through second slots in the lateral shell and adjustably securable at its opposite end to said buckling means, and one or more leg straps affixed at one end to the upper portion of a side shell and adjustably secured at its opposite end to said upper portion of the medial shell.

15. A therapeutic ankle orthosis according to claim 14 wherein the lateral shell is movable up and down and forwardly and rearwardly with straps comprising the cross-strap mechanism sliding in their respective lateral shell first and second slots to locate the medial shell in a selected position relative to a user's fibular malleolus.

16. A therapeutic ankle orthosis according to claim 14 wherein the straps comprising the cross-strap mechanism are affixed to the underside of the lateral side of the foot shell.

17. A therapeutic ankle orthosis according to claim 14 wherein the buckling means securing the ends of the first and second straps overlies the medial shell aperture.

18. A therapeutic ankle orthosis comprising:
 (a) an extended lateral shell having an aperture adapted to receive the fibular malleolus and having a lower end portion extending downwardly beneath that aperture;
 (b) a foot shell adapted to underlie the rear foot and having an upper medial side portion extending upwardly to overlap the lower end portion of the medial shell;
 (c) pivot means connecting the lower end portion of the medial shell to the side portion of the foot shell permitting angular movement of the foot shell relative to the medial shell about an axis substantially coincident with the functional axis of the talocrual joint, and
 (d) locking means for selectively preventing angular movement of the foot shell relative to the lateral shell comprising:
  (i) a curved slot formed in one of the overlapping medial shell lower end portions and foot shell side portion, the curve of the slot being centered about the axis of the pivot means, and one end of the slot being approximately horizontally forward of the pivot means axis and the other end of the slot being at least about 45° downwardly of the pivot means axis when the orthosis is positioned on the leg and foot and said leg and foot are positioned vertically and horizontally, respectively;
  (ii) removable locking screws extending through the slot at each end thereof into threaded engagement with the other of the overlapping medial shell lower end portions and foot shell side portion; and
 (e) adjustable strap means for holding the shells in operative position on the leg and ankle and foot and for applying focal compression to control edema of the ankle.

19. A therapeutic ankle orthosis according to claim 18 wherein the slot is formed in the medial shell lower end portion, said lower end portion overlapping the foot shell side portion, and the removable locking screws are in threaded engagement with the foot shell side portion.

20. A therapeutic ankle orthosis comprising:
 (a) an extended lateral shell having a positioning aperture corresponding to the fibular malleolus and having a lower end portion extending downwardly beneath that aperture and having a vertical molded channel therein;
 (b) a foot shell adapted to underlie the rear foot and having an upper medial side portion extending upwardly to overlap the lower end portion of the medial shell;
 (c) pivot means connecting the lower end portion of the medial shell to the upper side portion of the foot shell permitting angular movement of the foot shell relative to the medial shell about an axis substantially coincident with the functional axis of the talocrual joint, and (d) securing means for holding together the overlapping medial shell lower end portion and the foot shell side portion forwardly of the pivot means to resist ankle inversion and eversion comprising:

(i) a curved slot formed in one of the overlapping medial shell lower end portions and foot shell side portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on the leg and foot and said leg and foot are positioned vertically and horizontally, respectively;

(ii) a post affixed to the other of the overlapping medial shell lower end portions and the foot shell side portion, the post extending through the slot intermediate the ends thereof when the leg and foot are vertical and horizontal, respectively; and (iii) a cap on the outer end of the post for holding that shell portion in which the slot is formed against the other shell portion; and (e) adjustable strap means for holding the shells in operative position on the leg and ankle and foot, and for applying focal compression to control edema of the ankle.

21. A therapeutic ankle orthosis according to claim 20 wherein the slot is formed in the medial shell lower end portion, the lower end portion overlaps the foot shell side portion, and the post is affixed to the foot shell side portion.

22. A therapeutic ankle orthosis comprising:

(a) an extended lateral shell having a positioning aperture corresponding to the fibular malleolus and having a lower end portion extending downwardly beneath that aperture;

(b) a rigid extended medial shell adapted to fit beneath and upwardly about the tibial malleolus;

(c) a foot shell adapted to underlie the rear foot and having an upper lateral side portion extending upwardly to overlap the lower end portion of the medial shell;

(d) adjustable strap means for holding the shells in operative position on the leg and ankle and foot comprising:

(i) a strap fixed at one end to a forward portion of the foot shell and threaded through first slots in the lateral shell and adjustably secured at its opposite end to buckling means above the overlapping shell portions, a second strap fixed at one end to a rearward portion of the foot shell and threaded through second slots in the lateral shell one or more leg straps affixed at one end to the to upper portion of a side shell and adjustably secured at its opposite end to said upper portion of a shell.

23. A therapeutic ankle orthosis according to claim 22 wherein the lateral shell is movable up and down and forwardly and rearwardly with the straps comprising the cross-strap mechanism sliding in their respective lateral shell slots to locate the lateral shell in a selected position relative to a user's fibular malleolus.

24. A therapeutic ankle orthosis according to claim 22 wherein the straps comprising the cross-strap mechanism are affixed to the underside of the lateral side of the foot shell.

25. A therapeutic ankle orthosis according to claim 22 wherein the buckling means securing the ends of the first and second straps overlies the medial shell aperture.

26. A therapeutic ankle orthosis comprising:

(a) a rigid lateral shell having a positioning aperture corresponding to the fibular malleolus and having a lower end portion extending downwardly beneath that aperture, the lateral shell being contoured generally to fit the lower leg and ankle;

(b) a U-pad disposed beneath and upwardly about the aperture of the lateral shell and releasably secured to the inside of the lateral shell;

(c) a rigid extended medial shell adapted to fit beneath and upwardly about the tibial malleolus;

(d) a pad covering and being releasably secured to the inside of the medial shell;

(e) a foot shell adapted to underlie the rear foot and having an upper medial side portion extending upwardly to overlap behind the lower end portion of the medial shell;

(f) pivot means connecting the lower end portion of the medial shell to the upper side portion of the foot shell permitting angular movement of the foot shell relative to the lateral shell about an axis substantially coincident with the functional axis of the talocrural joint, the pivot means comprising a rivet fixed to the foot shell side portion and extending outwardly through a hold in the overlapping medial shell lower end portion and having a head holding the overlapping side and end shell portions together;

(g) a curved slot formed in the overlapping medial shell lower end portion, the curve of the slot being centered about the axis of the pivot means, one end of the slot being approximately horizontally forward of the pivot means axis and the other end of the slot being at least about 45° downwardly and forwardly of the pivot means axis when the orthosis is positioned on the leg and foot and said leg and foot are positioned vertically and horizontally, respectively;

(h) locking means for selectively preventing angular movement of the foot shell relative to the medial shell comprising removable locking screws extending through the slot at each end thereof into threaded engagement with the overlapping foot shell side portion;

(i) securing means for holding together the overlapping lower end portion of the medial shell and the side portion of the foot shell forwardly of the pivot means to resist ankle inversion and eversion comprising a post affixed to the foot shell side portion and extending through the slot intermediate the ends thereof when the orthosis is positioned on the leg and foot and said leg and foot are positioned vertically and horizontally, respectively, and a cap on the outer end of the post for holding the lateral shell lower end portion against the foot shell side portion; and (j) adjustable strap means for holding the shells in operative position on the leg and ankle and foot.

27. A therapeutic ankle orthosis according to claim 26 wherein the strap means comprises a strap fixed at one end to a forward portion of the foot shell and threaded through slots in the lateral shell secured at its opposite end to buckling means above the overlapping shell portions, a second strap fixed at one end to a rearward portion of the foot shell and threaded through slots in the lateral shell and turned back upon and adjustably secured to itself, and one or more leg straps affixed at one end to the upper portion of the lateral shell and adjustably secured at its opposite end to said upper portion of the medial shell.

28. A therapeutic ankle orthosis comprising:
(a) a first semi-rigid lateral side shell and a second semi-rigid medial side shell adapted to fit in operative position against the ankle of a user;
(b) said lateral side shell having a positioning aperture corresponding to a malleolus of the user;
(c) a U-pad releasably secured to the inside of said lateral shell to be disposed beneath and upwardly about the aperture of the shell;
(d) a foot shell adapted to underlie the rear foot of the user and having an upper side portion extending upwardly to overlap and connect to a lower end portion of said medial side shell; and
(e) adjustable strap means for holding the lateral side shell and pad in said operative position against the ankle comprising a first strap fixed at one end to a forward portion of the foot shell and threaded through first slots in the side shell and adjustably secured at its opposite end to securing means above the overlapping shell portions, and a second strap fixed at one end to a rearward portion of the foot shell and threaded through second slots in the lateral side shell and adjustably secured at its opposite end to said securing means.

29. A therapeutic ankle orthosis comprising:
(a) two extended side shells having an aperture adapted to receive a malleolus and having a lower end portion extending downwardly beneath that aperture;
(b) a foot shell adapted to underlie the rear foot and having an upper side portion extending upwardly to overlap the lower end portion of the side medial shell;
(c) pivot means connecting the lower end portion of the side medial shell to the side portion of the foot shell permitting angular movement of the foot shell relative to the side shell about an axis substantially coincident with the functional axis of the talocrural joint;
(d) locking means for selectively preventing angular movement of the foot shell relative to the side shell;
(e) securing means for holding together the overlapping lower end portion of the side shell and the side portion of the foot shell forwardly of the pivot means to resist ankle inversion and eversion; and
(f) adjustable strap means for holding the shells in operative position on the ankle and foot comprising a strap fixed at one end to a forward portion of the foot shell and threaded through slots in the side shell and a second strap fixed at one end to a rearward portion of the foot shell and threaded through slots in the side shell and adjustably secured at its opposite end to said securing means.

30. A therapeutic ankle orthosis comprising:
(a) an extended lateral shell having a vertical molded channel therein to facilitate edema drainage and a positioning aperture corresponding to the fibular malleolus and having a lower end portion extending downwardly beneath that aperture;
(b) an extended medial shell adapted to fit beneath and upwardly about the tibial malleolus;
(c) a foot shell adapted to underlie the rear foot and having an upper medial side portion extending upwardly to overlap the lower end portion of the medial shell;
(d) securing means for holding together the overlapping lower end portion of the medial shell and the side portion of the foot shell; and
(e) adjustable strap means for holding the shells in operative position on the leg and ankle and foot and for applying focal compression to control edema of the ankle.

31. The therapeutic ankle orthosis of claim 30 including a means for connecting and pivoting the lower end portion of the medial shell pivot means connecting the lower end portion of the medial shell to the side portion of the foot shell permitting angular movement of the foot shell relative to the medial shell about an axis substantially coincident with the functional axis of the talocrural joint.

32. The therapeutic ankle orthosis of claim 30 wherein the lateral shell is movable up and down and forwardly and rearwardly with straps comprising the cross-strap mechanism sliding in their respective lateral shell slots to locate the lateral shell in a selected position relative to a user's fibular malleolus.

33. A therapeutica ankle orthosis comprising
(a) a contoured extended lateral shell having a positioning aperture corresponding to the fibrular malleolus, a vertical channel therein to facilitate edema drainage and having a lower end portion extending downwardly beneath that aperture and having a vertical molded channel therein;
(b) an extended medial shell adapted to fit beneath and upwardly about the tibial malleolus;
(c) a foot shell adapted to underlie the rear foot and having an upper medial side portion extending upwardly to overlap the lower end portion of the medial shell;
(d) securing means for holding together the overlapping lower end portion of the medial shell and the side portion of the foot shell; and
(e) adjustable strap means for holding the shells in operative positive on the leg and ankle and foot for applying focal compression to control edema of the ankle, provided said securing means contains at least one adjustably securable strap through a D-ring and having a stapping arrangement to prevent the lateral shell from being displaced outwardly.

* * * * *